United States Patent [19]

Dhaliwal

[11] Patent Number: 5,591,425

[45] Date of Patent: Jan. 7, 1997

[54] TWO-PACKAGE PRETREATMENT AND HAIR RELAXER COMPOSITIONS

[75] Inventor: Tehsel Dhaliwal, Carrollton, Tex.

[73] Assignee: Pro-Line Corporation, Dallas, Tex.

[21] Appl. No.: 407,698

[22] Filed: Mar. 23, 1995

Related U.S. Application Data

[63] Continuation-in-part of Ser. No. 272,042, Jul. 8, 1994, abandoned.

[51] Int. Cl.$^6$ ................................ A61K 7/06; A61K 7/09
[52] U.S. Cl. ...................... 424/70.4; 424/70.2; 424/70.16
[58] Field of Search ............................ 424/70.11, 70.16, 424/70.17, 70.4, 70.28, 70.2; 132/204, 205

[56] References Cited

U.S. PATENT DOCUMENTS

| | | | |
|---|---|---|---|
| 4,175,572 | 11/1979 | Hsiung et al. | 132/7 |
| 4,524,787 | 6/1985 | Khalil et al. | 132/7 |
| 5,060,680 | 10/1991 | Akhtar | 132/204 |
| 5,068,101 | 11/1991 | Akhtar | 424/71 |
| 5,148,822 | 9/1992 | Akhtar | 132/204 |
| 5,148,829 | 9/1992 | Akhtar | 132/204 |
| 5,296,218 | 3/1994 | Chen | 424/70 |

*Primary Examiner*—Sallie M. Gardner
*Attorney, Agent, or Firm*—Jerome J. Norris

[57] ABSTRACT

A two-package pretreatment and hair relaxer system comprising: a first package comprising a neutral pretreatment composition containing a polyampholyte terpolymer having a weight average molecular weight of from about 4 thousand to 4 million, of the formula:

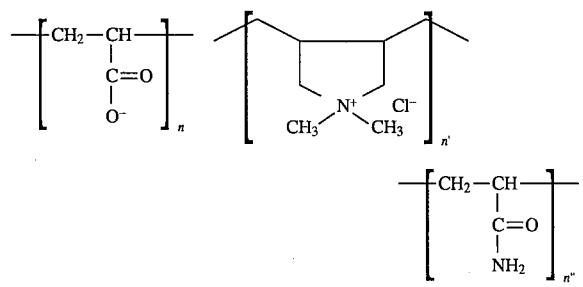

wherein said polyampholyte terpolymer is present in amounts sufficient to coat hair and prevent excessive brittleness and roughness to relaxed hair; and a second package containing calcium hydroxide in amounts sufficient to relax hair and a polyampholyte terpolymer having a weight average molecular weight of from about 4 thousand to 4 million, of the formula:

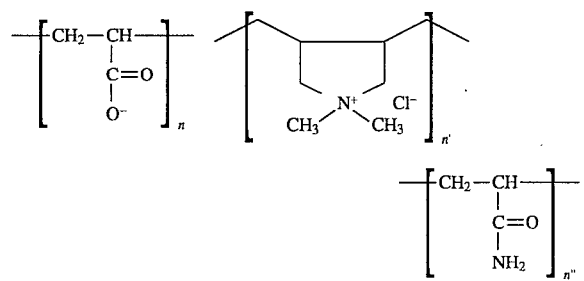

in amounts sufficient to impart significant amounts of moisture, softness and sheen to relaxed hair.

12 Claims, No Drawings

TWO-PACKAGE PRETREATMENT AND HAIR RELAXER COMPOSITIONS

BACKGROUND OF THE INVENTION

1. Field of the Invention

The present invention is a continuation-in-part of U.S. patent application Ser. No. 08/272,042, filed Jul. 8, 1994, now abandoned and relates to two-package pretreatment and hair relaxer compositions which provide higher amounts of moisture (as measured by superior softness), better sheen, and improved straightening when using the two-package compositions of the invention compared to prior art compositions. More particularly, the invention relates to two-package pretreatment and hair relaxer compositions in which the:

1) pretreatment composition is a non-alkaline (neutral or acidic) pretreatment composition containing a polyampholyte terpolymer having a weight average molecular weight of from about 4 thousand to 4 million, and recurring units of a five-membered nitrogen heterocyclic ring in the absence of highly alkaline conditions (pH 6.0–6.5), said terpolymer having repeating units of the formula:

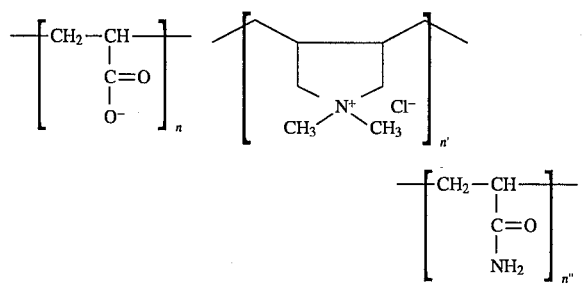

where n is 0.34; n' is 0.31; and n" is 0.35.

This polyampholyte terpolymer consist of 25% by weight of acrylic acid, 50% by weight of the repeating unit of the five-membered nitrogen heterocyclic ring, and 25% by weight of acrylamide; and 2) The no-lye relaxer composition comprises calcium hydroxide and a polyampholyte terpolymer having a weight average molecular weight of from about 4 thousand to 4 million, of the formula:

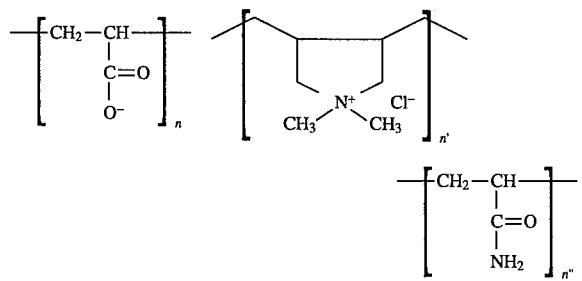

where n is 0.34; n' is 0.31; and n" is 0.35

This high molecular weight polyampholyte terpolymer consists of 25% by weight acrylic acid, 50% by weight of the recurring units of the five-membered nitrogen heterocyclic ring, and 25% by weight of acrylamide.

2. The Prior Art

In the hair relaxing or straightening art, it is known that sodium hydroxide containing compositions induce pH values of between about 12 to about 14 in the presence of water, and that these sodium hydroxide containing compositions have been formulated as emulsified or viscous compositions that will not drip onto the skin or in the eyes after application to a user's hair.

In general, hair relaxers have been prepared as "no-base" formulations or "with base" formulations.

The "with base" formulation is supplied in two separate packages—one containing a oleaginous base and one which contains a thick aqueous composition containing the sodium hydroxide or lye. In application, the "with base" formulation is applied in a manner so that the oleaginous package or mix is applied first as a protective layer to the scalp and hair of the user. Thereafter, the thickened aqueous sodium hydroxide or lye containing creme mixture is applied to relax or straighten the hair.

On the other hand, the "no-base" formulations are single package systems in which the oleaginous materials and the sodium hydroxide or lye containing materials are co-emulsified. In the "no-base" formulation systems, the formulations are directly applied to the user's hair without prior treatment of the hair and scalp.

Although advances have been made in preparing "no-base" compositions so that the risk of dripping the composition into the eyes or injuring the scalp are lessened, there is nevertheless a tendency for the "no-base" compositions to separate or de-emulsify and loose stability because of the two distinct phases of the product; namely, the pretreatment phase and the conditioning phase.

Disadvantages associated with the separation or deemulsification of the "no-base" composition is that the active ingredients will not be present in the proper proportions and will therefore cause uneven relaxation with retained roughness in some areas of the hair and therefore result in user dissatisfaction and complaints.

Sodium hydroxide containing hair straightening or relaxer compositions have been known for some time, and a significant number of hair straightening or relaxer compositions are based on sodium hydroxide. The sodium hydroxide based relaxers usually contain petrolatum and/or mineral oil to moderate or reduce the alkaline or caustic effect and anionic surfactants and non-ionic surfactants that provide better wettability of the sodium hydroxide-based straightening or relaxer composition.

The chief disadvantage of sodium hydroxide-based relaxers is that the hair is left in a brittle condition and is coarse or harsh to touch. Nevertheless, sodium hydroxide relaxers have many advantages over the more recent sulfite or thioglycolate relaxing agents in that the sodium hydroxide relaxers do not have the repulsive odors created by the sulfite or thioglycolate action in reducing the hair, because sodium hydroxide straightened hair is already cross-linked by a lanthionine linkage, and it is only necessary following the relaxing or straightening process to treat the hair with an acidic shampoo in order to remove the excess alkaline solution.

Another disadvantage attendant to using reducing agents such as sulfites or thioglycolates to react with the disulfite bond of hair keratin to form sulfhydryl or reduced hair is that the use of these reducing agents require the further use of an oxidizing neutralizer, i.e., hydrogen peroxide for purposes of recreating the disulfite linkages and thereby ending the straightening process. After the oxidizing neutralizer is removed, the relaxation or straightening process is followed by shampooing.

In the hair care treatment area of relaxation and straightening, there has been considerable recent activity as well as demand for products which will condition and relax the hair and yet leave the hair soft and manageable in the straightened or curly state, and towards these ends, a number of water soluble quaternary, cationic polymers capable of modifying hair surfaces and improving its condition have been incorporated in hair waving and straightening compositions, whether based on reducing agents having the capacity to reduce the disulfite linkages in hair keratin or sodium hydroxide or calcium hydroxide based hair conditioning and straightening compositions.

However, these water soluble quaternary, cationic polymers normally capable of modifying the surface characteristics of hair and improving its condition so that the hair is less brittle and softer to the touch are also known not to function effectively for these purposes when employed in highly alkaline solutions.

Therefore, a need exist in the hair conditioning and relaxation or straightening art to provide a no-lye, less alkaline composition which, when used together with a given water soluble polymer will prevent overprocessing during the relaxation or straightening process so that split ends and damaged hair which gives a brittle or harsh feeling to the touch is substantially lessened, and softness and high sheen or a reflectance is provided.

U.S. Pat. No. 4,175,572 discloses a hair conditioning composition for use under highly alkaline conditions that include mineral oil, non-ionic emulsifiers and from about 0.05 to about 20 weight percent of a quaternary polymer having recurring units of the formula:

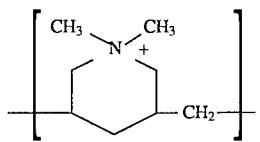

U.S. Pat. No. 4,524,787 is directed to a hair relaxer system in at least two packages, wherein the first package contains a water-free activator and a second package contains water. The active ingredient in the first package is a hydrolyzable organic base of guanidine.

U.S. Pat. No. 5,060,680 discloses an aqueous hair texturing and strengthening composition for use on hair undergoing an alkaline straightening procedure, wherein the composition includes 0.1 to 8% by weight of at least one water-dispersible hair texturing and strengthening agent including a quaternary nitrogen atom with at least one aliphatic alkyl group directly or indirectly bonded to the quaternary nitrogen atom, wherein the aliphatic alkyl group has from 3 to 22 carbon atoms, and from 0 to 5% of a water-dispersible cationic polymer, having repeating units of a six-membered nitrogen heterocyclic ring. The copolymer contains 5 parts of acrylic acid and 95 parts of dimethyldiallylammonium chloride.

U.S. Pat. No. 5,068,101 discloses a method of preparing a highly alkaline oil-and-water emulsion cream, in which a polymeric quaternary nitrogen conditioning agent is included.

U.S. Pat. No. 5,148,822 discloses hair texturing and strengthening compositions for hair about to undergo a highly alkaline hair straightening procedure. The composition contains 0.1 to about 8 weight percent of at least one water-dispersible quaternary nitrogen-containing compound having at least one alkyl group directly or indirectly bonded to a quaternary nitrogen group, wherein each alkyl group contains 3 to 22 carbon atoms.

However, there is a need to provide a no-lye or non-sodium hydroxide based relaxer or hair straightening composition to eliminate the brittle condition and harsh touch associated with hair relaxed or straightened using this reagent and yet avoid the disadvantages associated with using calcium hydroxide as the active ingredient or relaxer in an emulsion, in which the calcium hydroxide can partially dry and form a solid calcium compound on the surface of the emulsion, or create pastiness when used along with an oleaginous material in combination with water soluble quaternary, cationic polymers in an attempt to modify the surface characteristics of the hair and improve the condition of the hair after the relaxation or straightening process.

SUMMARY OF THE INVENTION

One object of the invention is to provide a two-package pretreatment and hair relaxer composition that provides higher amounts of moisture, (as measured by superior softness), better sheen, and improved straightening, when compared to prior art compositions, by providing a non-alkaline pretreatment composition containing a polyampholyte terpolymer having a weight average molecular weight of from about 4 thousand to 4 million, and repeating units of the formula:

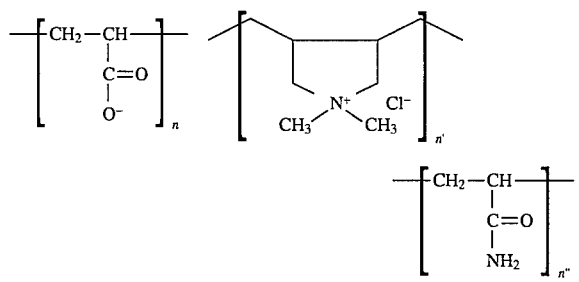

wherein n is 0.34; n' is 0.31; and n" is 0.35

Another object of the invention is to provide a pretreatment composition containing the mentioned polyampholyte terpolymer, that lessens brittleness and roughness to relaxed or straightened hair, as a result of the pretreatment composition not being interfered with due to a lack of alkalinity.

A yet further object of the invention is to provide a no-lye calcium hydroxide relaxer composition that also contains a polyampholyte terpolymer having a weight average molecular weight of from about 4 thousand to 4 million, and repeating units of the formula:

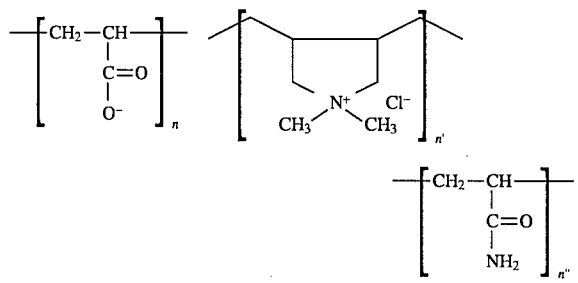

wherein n is 0.34; n' is 0.31; and n" is 0.35

A still further object of the invention is to provide a two-package pretreatment and relaxer hair care composition which provides higher amounts of moisture or softness, better sheen, and superior straightening characteristics after successive pretreatment and relaxer applications, in which both the neutral pretreatment composition and the no-lye calcium hydroxide relaxer or straightening composition contain a polyampholyte terpolymer having a weight average molecular weight of from about 4 thousand to 4 million, and repeating units of the formula

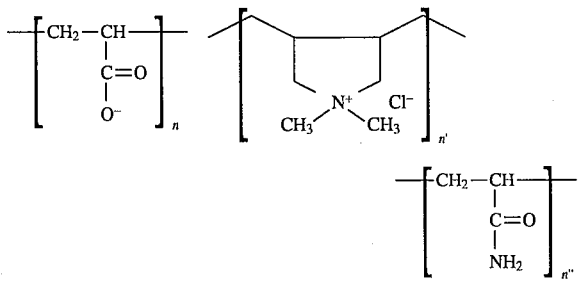

wherein n is 0.34; n' is 0.31; and n" is 0.35
wherein the polyampholyte terpolymer contains 25% by weight of acrylic acid, 50% by weight of the moiety containing the 5-membered nitrogen heterocyclic ring, and 25% acrylamide.

A further object yet still of the invention is to provide a two-package pretreatment and relaxer hair care composition, which upon distribution of the neutral pretreatment composition over the hair and subsequent application of the no-lye calcium hydroxide alkaline creme relaxer composition to about one-quarter inch sections of parted hair for a period of from about 10 to about 20 minutes, imparts higher amounts of moisture or softness, superior sheen, and improved straightening, upon rinsing and drying the hair.

In general, the neutral non-alkaline pretreatment composition will comprise on a weight basis:

| | |
|---|---|
| [1]POLYMER JR-30 ® (Trimethyl ammonium substituted epoxide) | 0.5 |
| Hydroxy ethyl cellulose | 0.06 |
| Propylene Glycol | 8.0 |
| Polyampholyte terpolymer | 6.0 |
| Dicetyl Dimonium Chloride | 0.5 |
| [2]TEA-Cocoyl Hydrolyzed Collagen | 0.1 |
| Sodium salt of pyroglutamic acid | 0.1 |
| [3]Polysorbate 20 | 0.12 |
| Fragrance | 0.02 |
| Methylchloroisothiazalinone | 0.04 |
| Deionized water | Balance to 100% |

[1]Cationic cellulose ether as defined in U.S. Pat. No. 3,992,336.
[2]TEA-Cocoyl Hydrolyzed Collagen is the triethanolamine salt of the condensation product of coconut acid chloride and Hydrolyzed Collagen (q.v.).
[3]Mixture of laurate esters of sorbital and sorbitol anhydrides, consisting predominately of the monoester, condensed with approximately 20 moles of ethylene oxide.

The no-lye calcium hydroxide relaxer composition will comprise on a percent by weight basis:

| | |
|---|---|
| Calcium hydroxide | 5.8 |
| Propylene glycol | 5.0 |
| [4]PEG-75-lanolin | 4.0 |
| Nonoxnol-10-carboxylic acid | 1.0 |
| Polyampholyte terpolymer | 1.1 |
| Mineral oil | 11.0 |
| Petrolatum | 16.0 |
| [5]DEA Oleth-3 Phosphate | 0.25 |
| [6]Lipowax P | 8.0 |
| Cetearyl alcohol | 5.38 |
| Stearyl alcohol | 0.77 |
| Fragrance | 0.3 |
| Deionized water | Balance to 100% |

[4]Polyethylene glycol derivative of lanolin with average of 75 moles of ethylene oxide.
[5]Diethanolamine salt of mixture of esters of phophoric acid and Oleth-3.
[6]Mixture of Cetearyl Alcohol (and) Polysorbate 60.

In order to insure that the non-alkaline pretreatment or pre-relaxer composition prevents overprocessing of the hair upon placing the relaxer on the hair, preparation of the pretreatment composition is obtained by the process of placing deionized water into a vessel and heating until the water is about 65° C. Mixing Polymer JR-30® (Trimethyl ammonium substituted epoxide); hydroxy ethyl cellulose and propylene glycol, and adding this mixture to the deionized water with mixing until a solution is formed. Adding the polyampholyte terpolymer, dicetyl dimonium chloride and TEA-Cocoyl Hydrolyzed Collagen with mixing and cooling the mixture to about 40° C. While keeping the temperature at about 40° C. polysorbate 20, fragrance and methylchloroisothiazalinone are added with stirring for about 15 minutes, and the temperature is lowered to about 35° C. to obtain a solution having a pH of approximately 6.0 to about 6.5.

The no-lye, calcium hydroxide relaxer cream is prepared by adding deionized water to a vessel and then adding calcium hydroxide with mixing until it is completely dissolved. Thereafter, propylene glycol, PEG-75-lanolin, nonoxinol-10-carboxylic acid and the polyampholyte terpolymer and mineral oil are added with stirring. Next, petrolatum, DEA Oleth-3 phosphate, LIPO P, Cetearyl alcohol, and stearyl alcohol are added with stirring until the temperature reaches about 85° C., whereupon mixing is continued for about 30 minutes. Thereafter, fragrance is added with mixing, whereupon the no-lye relaxer composition cream has a pH at 25° C. which measures from about 11.7 to about 12.3.

DETAILED DESCRIPTION OF THE INVENTION

The two-package pretreatment and hair relaxer compositions of the invention coact to provide higher amounts of moisture or softness, superior sheen, and improved straightness to relaxed or straightened hair after successive pretreatment and relaxer applications.

The lye or sodium hydroxide base used to relax or straighten hair tends to leave the relaxed or straightened hair with a rough feel due to uneven straightening and the tendency to produce split ends. A pretreatment composition is designed to coat and protect the hair and scalp, and to prevent the hair from being overprocessed, as it lessens the harshness of the lye or sodium hydroxide base. The pretreatment composition typically contains water soluble quaternary, cationic polymers which modify the surface characteristics of the hair; however, these cationic polymers tend to be employed effectively towards these ends in aqueous compositions that are not highly alkaline.

The present invention utilizes a pretreatment or preconditioning hair treatment composition in which the pH range is almost neutral or in a range of from about 6.0 to about 7.0. In this pH range, it has been found that when a high molecular weight polyampholyte terpolymer having a weight average molecular weight of from about 4 thousand to 4 million, and recurring units of the formula:

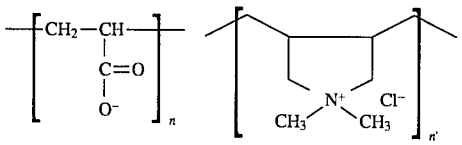

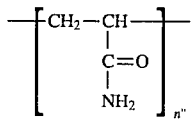

wherein n is 0.34; n' is 0.31; and n" is 0.35 is employed in the pretreatment formulation, the pretreatment formulation will prevent over processing of the hair when a no-lye, calcium hydroxide relaxer composition is subsequently used to straighten the hair.

The pre-relaxer hair treatment composition of the invention further provides strength to damaged, unconditioned hair, repairs and prevents split ends in both damaged and previously overprocessed hair, adds moisture to the hair, makes the relaxer application easier, and penetrates the hair shafts so that hair after treatment with the no-lye, calcium hydroxide relaxer composition is relaxed hair with a greater moisture content, greater softness to the touch, and more capability of reflecting light as a result of its greater sheen or luster.

The amount of polyampholyte terpolymer useful to provide conditioning and sufficient wettability to the hair in the non-alkaline pretreatment composition will range from about 5 to about 10% by weight of the pretreatment composition; preferably from about 6 to 9% by weight of the pretreatment composition; and most preferably about 8% by weight of the pretreatment composition. When the polyampholyte terpolymer is used in the foregoing amounts together with surfactants, fragrances, and other wetting agents, the pre-relaxer treatment provides the advantages of: preventing overprocessing; strengthening damaged, unconditioned hair; repairing and preventing split ends of hairs; adding moisture to the hair; making the relaxer application easier to apply; and penetrating the hair shafts so that the action of the relaxer or straightening composition commences immediately, thereby lessening the period of time that the relaxer or straightener composition needs to remain in the hair.

The pretreatment composition is obtained by placing deionized water into a vessel and heating the water until it reaches about 65° C. Polymer JR-30® (Trimethyl ammonium substituted epoxide) hydroxy ethyl cellulose and propylene glycol are then mixed, and this mixture is added to the deionized water to form a solution. The polyampholyte terpolymer, dicetyl dimonium chloride and TEA-Cocoyl Hydrolyzed Collagen are mixed next and this mixture is cooled to about 40° C. While keeping the temperature at about 40° C., polysorbate 20, fragrance and methylchloroisothiazalinone are added with stirring for about 15 minutes. Thereafter, the temperature is lowered to about 35° C. and this mixture is added to the previous mixture to obtain a solution having a pH of approximately 6.0 to about 7.0.

The no-lye, calcium hydroxide relaxer or straightening composition is less harsh than a sodium hydroxide based relaxer composition as it has less of a tendency to leave the hair in a roughened, non-glossy or low-sheen condition; however, the use of calcium hydroxide as the active ingredient in the relaxer or straightening composition causes calcium products to precipitate out in the relaxing composition and onto the strands of relaxed or straightened hair. Moreover, even before the relaxer or straightening composition containing calcium hydroxide as the active ingredient is placed on the hair, there is a tendency for the calcium hydroxide to become partially dry and "skin over" because the formation of solid calcium on the surface of the emulsion.

The aforementioned disadvantages attendant to the use of calcium hydroxide as the active ingredient in the no-lye, relaxer composition are eliminated by incorporating the polyampholyte terpolymer into the no-lye calcium hydroxide relaxer composition.

The amount of polyampholyte terpolymer that is useful in the no-lye relaxer composition may range from about 0.5 to about 1.5% by weight; preferably from about 0.8 to about 1.2; most preferably about 1.1% by weight.

The no-lye calcium hydroxide relaxer composition is prepared by adding deionized water to a vessel and adding calcium hydroxide with mixing until it is completely dissolved. Thereafter, propylene glycol, PEG-75-lanolin, Nonoxynol-10-carboxylic acid and the polyampholyte terpolymer and mineral oil are added to the calcium hydroxide solution with stirring. Next, petrolatum, DEA Oleth-3 phosphate, LIPO P, Cetearyl alcohol, and stearyl alcohol are added to the previous mixture with stirring until the temperature reaches about 85° C., whereupon mixing is continued for about 30 minutes. Thereafter, fragrance is added with mixing to form a no-lye relaxer composition cream having a pH at 25° C. which measures about 11.5 to 11.7.

Because of the inclusion of the polyampholyte terpolymer, the pretreatment composition is not required to be alkaline, but instead may be neutral or acidic, and the neutral or acidic pretreatment composition does not prevent or interfere with the capability of the nonionic polyampholyte terpolymer to provide protection against hair overprocessing once the relaxer composition is applied.

Further, the inclusion of the polyampholyte terpolymer in the no-lye, calcium hydroxide containing relaxer or straightening composition prevents the calcium hydroxide from becoming partially dry and "skinning over" due to the tendency for calcium hydroxide to form a solid calcium compound on the surface of the emulsion. The formation of a solid calcium compound on the surface of the emulsion or creme of the relaxer or straightening composition would create an uneven distribution of the calcium hydroxide active ingredient in the composition per se and thereby prevent even or uniform relaxation or straightening of the hair.

Accordingly, the polyampholyte terpolymer provides valuable functions in both the pretreatment as well as the relaxer or straightening compositions in the two-package pretreatment and hair relaxer compositions of the invention.

In applying the pretreatment composition of the invention, the composition may be placed in the palm of the hand and distributed over the hair and throughout the ends of the hair until the hair is thoroughly wetted. While the hair is wetted with the neutral pre-relaxer or conditioner treatment solution, the shoulders of the user should be covered with a towel, and the hair should be carefully detangled with a large tooth comb. Thereafter, the hair is parted into four sections, from ear to ear and down the center. Next, a protective gel is applied around the entire forehead, neck and ears prior to treatment with the relaxer or straightening composition. Beginning at the back section of the head, the hair is parted into one-fourth inch sections and a generous amount of the relaxer is applied with the back of a wide tooth comb about one-half of an inch away from the scalp to about one-half an inch away from the ends of the hair and the relaxer composition is moved through the hair until each one-quarter inch section is complete, before moving to the next one-quarter inch section.

The length of time in which the relaxer composition is kept in each section will vary from about 10 to about 20 minutes, depending upon the hair texture. For relatively fine hair texture, the maximum time in which the relaxer is kept in the hair will range from about 10 to about 12 minutes. For medium texture hair, the amount of time in which the relaxer will remain in the hair will range from about 12 to about 15 minutes. While for coarse hair texture, the amount of time in which the relaxer or straightener will remain hair will range from about 15 to about 20 minutes.

After the relaxer has remained in the hair for the recommended period of time, rinse-out with warm water and then a generous amount of a neutralizing shampoo capable of decalcifying and removing the build-up residue is placed into the treated hair and worked into a lather. A Color Code™ neutralizing and decalcifying shampoo may be used in order to indicate areas where the creme relaxer is not completely out of the hair by producing a pink colored lather. After the shampoo is fully worked into the hair, the hair should be rinsed well and the shampoo process repeated until all of the creme relaxer is removed, as indicated by the lack of production of the pink colored lather. When all of the creme relaxer is removed from the hair and around the ears, forehead and nap of the neck, the appearance of the lather will be white. At this point, the hair should be rinsed thoroughly.

The drying technique should be tailored to achieve the style desired from the relaxed hair. For roller sets, waves or wraps, it is recommended that a PERM REPAIR® VITA-PHLEX leave-in-condition be applied. After the setting lotion is applied, comb or set the hair in the desired style and sit under a hooded dryer until the hair is completely dry. Thereafter, the roller sets, waves or wraps are then removed.

For the full body look, a small amount of a creme moisturizer should be applied to the ends of the hair in order to obtain extra smoothness and control. The hair should be sectioned into four parts and secured by the use of a wide tooth comb or blow dryer attachment and then blown dry one section at a time. This drying technique is especially important for styling thin hair.

In order to obtain a style in which the curls are firm, after the set or curled hair is complete and dry, the rollers should be removed and the curls be sprayed with a holding spray and then styled as desired. A light mist of the holding spray may be applied again in burst for a longer lasting or firm curl type of styling.

EXAMPLE

Tests were run to evaluate and compare the effectiveness of two curl relaxer products under the parameters of softness, sheen, and straightening. The analysis was conducted in-vitro on hair swatches that were 2 grams in weight and 7 cm in length.

Negroid hair samples were received from Regines International Hair and Beauty Salon, Nyack, N.Y. Twenty swatches were selected for treatment using the relaxer composition of the present invention compared to 20 samples of the same swatches treated using a relaxer composition of the prior art which did not include the invention's polyampholyte terpolymer.

The conditioning hair relaxer of the prior art had the following compositional make-up:

| Ingredient | Weight Percent |
| --- | --- |
| Petrolatum | 26.0 |
| Mineral oil | 9.5 |
| Polyethylene (1500 M.W.) | 1.0 |
| Emulsifying Wax | 10.0 |
| Propylene glycol | 5.5 |
| Calcium hydroxide | 2.2 |
| Polyoxyethylene lanolin ether | 1.0 |
| Diallyldimethylammonium chloride-acrylamide copolymer | 0.5 |

-continued

| Ingredient | Weight Percent |
|---|---|
| Water to | 100.0 |

The following no-lye calcium hydroxide relaxer composition of the present invention was used as the basis for comparison:

| | |
|---|---|
| Calcium hydroxide | 5.8 |
| Propylene glycol | 5.0 |
| [7]PEG-75-lanolin | 4.0 |
| Nonoxynol-10-carboxylic acid | 1.0 |
| Polyampholyte terpolymer | 1.1 |

$$\left[ \begin{array}{c} CH_2-CH \\ | \\ C=O \\ | \\ O^- \end{array} \right]_n \quad \left[ \begin{array}{c} \phantom{xx} \\ N^+ \quad Cl^- \\ CH_3 \quad CH_3 \end{array} \right]_{n'} \quad \left[ \begin{array}{c} CH_2-CH \\ | \\ C=O \\ | \\ NH_2 \end{array} \right]_{n''}$$

| | |
|---|---|
| Mineral oil | 11.0 |
| Petrolatum | 16.0 |
| [8]DEA Oleth-3 Phosphate | 0.25 |
| [9]Lipowax P | 8.0 |
| Cetearyl alcohol | 5.38 |
| Stearyl alcohol | 0.77 |
| Fragrance | 0.3 |
| Deionized water | Balance to 100% |

[7]Polyethylene glycol derivative of lanolin with average of 75 moles of ethylene oxide.
[8]Diethanolamine salt of mixture of esters of phosphoric acid and Oleth-3.
[9]Mixture of Cetearyl Alcohol (and) Polysorbate 60.

1) Hair Softness

A DIA-STRON Rheometer (DIA-STRON Limited, Broomall, Pa.) was used to measure the softness response of the hair swatches. The Rheometer is a table top tensile-compression tester. The machine was adapted to gently squeeze the hair swatch between two flat surfaces. One surface was non-yielding while the other could be moved when subjected to a linear force. The linear force was developed by the hair as the non-yielding arm impinged upon the swatch. The maximum force generated was recorded as a measurement of the hair's elasticity or softness at that site.

The rheometer was programmed to insure that the relative closing distance was the same for each test subject, thereby assuring that equivalent distortional forces were applied throughout the group. Three repetitive readings were taken to compensate any variations introduced by swatch positioning.

Increases in grams of force applied to the hair swatches is translated as a reduction in resistance being offered by the swatch. The New Lexicon Webster's Dictionary of the English Language defines softness as "offering little resistance to pressure". Therefore, a reduction in resistance indicates a "softer" hair end product.

2) Hair Sheen

A FIBER LITE 3100 Light Source (Dolan-Jenner Industries, Wobum, Mass.) in conjunction with a SEKONIC DIGILITE Detector (Model L-318B) was used to determine the sheen of the hair swatches pre and post straightening treatment with the test products. Swatches were positioned at a fixed distance under a detector with the light source directed on from a fixed distance and constant angle. LUX measurements were taken and an increase in values is translated as an increase in the overall hair "sheen".

3) Hair Straightening

A MORITEX SCOPEMAN 503 at a magnification of 25× was used with a SONY TRINITRON monitor to measure the length of the hair swatches before and after treatment with the test materials. Increases in the length of the hairs is an indication of the straightening effectiveness of the treatment.

SOFTNESS DATA

Measurements via Diastron Rheometer in grams of force of resistance. Higher resistance represents "softer" hair.

| PRIOR ART | | | INVENTION COMPOSITION | | |
|---|---|---|---|---|---|
| SAMPLE NO. | PRE | POST | SAMPLE NO. | PRE | POST |
| 1 | 256.0 | 270.0 | 1 | 257.0 | 298.0 |
| 2 | 258.0 | 276.0 | 2 | 255.0 | 307.0 |
| 3 | 259.0 | 277.0 | 3 | 260.0 | 291.0 |
| 4 | 257.0 | 278.0 | 4 | 258.0 | 299.0 |
| 5 | 261.0 | 273.0 | 5 | 263.0 | 295.0 |
| 6 | 258.0 | 283.0 | 6 | 257.0 | 297.0 |
| 7 | 260.0 | 280.0 | 7 | 258.0 | 294.0 |
| 8 | 255.0 | 281.0 | 8 | 259.0 | 296.0 |
| 9 | 258.0 | 279.0 | 9 | 264.0 | 297.0 |
| 10 | 259.0 | 278.0 | 10 | 260.0 | 298.0 |
| 11 | 262.0 | 279.0 | 11 | 259.0 | 304.0 |
| 12 | 260.0 | 284.0 | 12 | 255.0 | 293.0 |
| 13 | 258.0 | 280.0 | 13 | 264.0 | 295.0 |
| 14 | 257.0 | 273.0 | 14 | 266.0 | 293.0 |
| 15 | 265.0 | 285.0 | 15 | 259.0 | 297.0 |
| 16 | 261.0 | 280.0 | 16 | 258.0 | 296.0 |
| 17 | 260.0 | 283.0 | 17 | 260.0 | 296.0 |
| 18 | 258.0 | 278.0 | 18 | 258.0 | 302.0 |
| 19 | 258.0 | 279.0 | 19 | 261.0 | 294.0 |
| 20 | 259.0 | 283.0 | 20 | 259.0 | 295.0 |
| MEAN: | 259.0 | 279.0 | MEAN: | 260.0 | 296.9 |
| | | 7.7% increase | | | 14.2% increase |

The invention composition was superior in softness when compared to the prior art composition.

SHEEN DATA

Measurements via Glossimetry in LUX units. Higher numbers represent greater effective "sheen" of hair.

| | PRIOR ART | | | INVENTION COMPOSITION | |
|---|---|---|---|---|---|
| SAMPLE NO. | PRE | POST | SAMPLE NO. | PRE | POST |
| 1 | 22.7 | 23.4 | 1 | 22.6 | 26.2 |
| 2 | 22.5 | 23.7 | 2 | 22.5 | 26.0 |
| 3 | 22.9 | 23.9 | 3 | 22.7 | 26.4 |
| 4 | 22.8 | 22.8 | 4 | 22.3 | 25.7 |
| 5 | 22.7 | 23.0 | 5 | 22.6 | 25.8 |
| 6 | 21.9 | 23.5 | 6 | 22.4 | 26.0 |
| 7 | 22.6 | 24.0 | 7 | 23.0 | 26.1 |
| 8 | 22.4 | 23.7 | 8 | 22.5 | 25.6 |
| 9 | 23.0 | 23.2 | 9 | 22.6 | 26.0 |
| 10 | 22.7 | 23.6 | 10 | 22.3 | 26.5 |
| 11 | 22.8 | 23.6 | 11 | 22.4 | 25.4 |
| 12 | 22.9 | 23.2 | 12 | 22.1 | 25.8 |
| 13 | 23.1 | 22.9 | 13 | 22.2 | 25.7 |
| 14 | 22.6 | 23.8 | 14 | 22.4 | 25.4 |
| 15 | 22.0 | 23.9 | 15 | 22.6 | 25.8 |
| 16 | 22.8 | 23.5 | 16 | 22.8 | 25.9 |
| 17 | 22.5 | 24.0 | 17 | 22.7 | 26.3 |
| 18 | 22.6 | 23.6 | 18 | 22.9 | 26.2 |
| 19 | 22.5 | 23.5 | 19 | 22.3 | 26.4 |
| 20 | 22.7 | 23.2 | 20 | 22.7 | 25.9 |
| MEAN: | 22.6 | 23.5 | MEAN: | 22.5 | 26.0 |
| | | 4.0% increase | | | 15.6% increase |

The invention composition was superior in increasing sheen when compared to the prior art composition. While it is not desired to be bound by any theory explaining why superior sheen is obtained using the no-lye conditioning creme relaxer of the invention composition, it is nevertheless believed that the terpolymer together with the nonoxynol-10-carboxylic acid operate to prevent residual or build-up calcium from coating the straightened or relaxed hair, by complexing or tying up the calcium.

STRAIGHTENING DATA

| | PRIOR ART | | | INVENTION COMPOSITION | |
|---|---|---|---|---|---|
| SAMPLE NO. | PRE | POST | SAMPLE NO. | PRE | POST |
| 1 | 6.7 | 7.1 | 1 | 6.9 | 7.5 |
| 2 | 7.0 | 7.5 | 2 | 7.3 | 7.8 |
| 3 | 6.9 | 7.0 | 3 | 6.2 | 6.4 |
| 4 | 7.7 | 7.9 | 4 | 7.1 | 7.8 |
| 5 | 7.3 | 7.4 | 5 | 7.4 | 7.7 |
| 6 | 7.8 | 8.0 | 6 | 7.5 | 8.0 |
| 7 | 6.6 | 6.9 | 7 | 6.7 | 7.0 |
| 8 | 7.2 | 7.4 | 8 | 7.2 | 7.6 |
| 9 | 7.3 | 7.7 | 9 | 6.4 | 7.0 |
| 10 | 6.4 | 6.5 | 10 | 7.4 | 7.9 |
| 11 | 7.1 | 7.5 | 11 | 6.9 | 7.4 |
| 12 | 7.2 | 7.5 | 12 | 6.6 | 7.0 |
| 13 | 6.8 | 7.4 | 13 | 7.8 | 8.3 |
| 14 | 7.0 | 7.6 | 14 | 7.3 | 7.6 |
| 15 | 6.6 | 7.0 | 15 | 7.7 | 8.1 |
| 16 | 7.4 | 7.7 | 16 | 6.8 | 7.4 |
| 17 | 7.6 | 8.1 | 17 | 7.5 | 7.8 |
| 18 | 7.4 | 7.8 | 18 | 7.6 | 7.9 |
| 19 | 6.3 | 6.6 | 19 | 6.9 | 7.5 |
| 20 | 7.7 | 8.0 | 20 | 7.2 | 7.7 |
| MEAN: | 7.1 | 7.4 | MEAN: | 7.2 | 7.6 |
| | | 4.2% increase | | | 7.0% increase |

The invention composition was superior in hair straightening when compared to the prior art composition.

It has been found that the polyampholyte terpolymers of the invention are capable of imparting the improved characteristics of softness, sheen, and straightening when used in the amounts prescribed in the pretreatment and relaxer components in the two-package composition system, when the cationic and anionic components are present in molar percent amounts so that the percent net charge of the overall polyampholyte terpolymer is between −2.5 and +2.5; however, in a preferred embodiment of the invention, it is desirable that the percent net charge be as close to 0 as is possible. To insure the improved characteristics obtained by use of the two-package composition of the invention, it is important that the pretreatment composition is non-alkaline or within a pH range of between about 6.0–6.5, and that the pH range of the relaxer or straightener composition containing the polyampholyte terpolymer be within the range of about 11.5 to about 11.7.

While the invention has been described generally with respect to the preferred embodiments, it will be appreciated by those skilled in the art that modifications or variations of the disclosed compositions and methods can be made without departing from the scope of the invention, which is defined by the claims which follow.

What is claimed is:

1. A two-package pretreatment and hair relaxer composition system comprising:

a first package comprising a non-alkaline pretreatment composition containing a polyampholyte terpolymer of the formula:

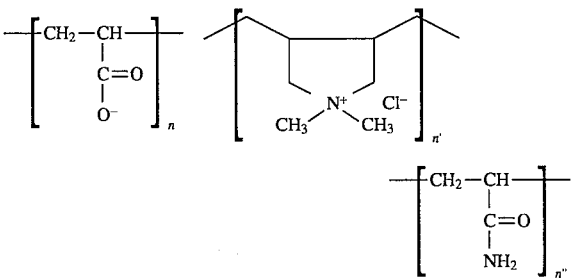

wherein n is 0.34; n' is 0.31; and n" is 0.35; said terpolymer having a weight average molecular weight of from about 4 thousand to 4 million, and being present in amounts sufficient to coat hair and prevent brittleness and roughness to relaxed hair;

a second package comprising a relaxer having an alkaline pH range of from about 11.5 to 11.7 containing calcium hydroxide in amounts sufficient to relax hair and a polyampholyte terpolymer of the formula:

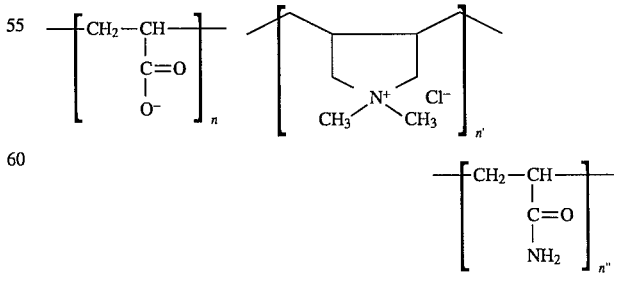

wherein n is 0.34, n' is 0.31; and n" is 0.35; said terpolymer having a weight average molecular weight of from about 4 thousand to 4 million, and being present in amounts sufficient to impart moisture, softness and sheen to relaxed hair; and wherein said second package further includes nonoxynol-10-carboxylic acid.

2. The hair relaxer composition system of claim 1, wherein the polyampholyte terpolymer present in the non-alkaline pretreatment composition of said first package is present in an amount from about 5 to about 10% by weight, and the amount of polyampholyte terpolymer in said second package is present in an amount from about 0.5 to about 1.5% by weight.

3. The hair relaxer system of claim 2, wherein the amount of polyampholyte terpolymer is present in amounts of from about 6 to about 9% of said first package, and the amount of polyampholyte terpolymer in said second package is present in an amount from about 0.8 to about 1.2% by weight in the second package.

4. The hair relaxer system of claim 3, wherein the amount of polyampholyte terpolymer is present in the amount of 6% by weight in the first package, and the amount of polyampholyte terpolymer present in the second package is 1.1% by weight.

5. The composition of claim 1, wherein the first package additionally includes Trimethylammonium substituted epoxide, Hydroxy ethyl cellulose, Propylene Glycol, Dicetyl Dimonium Chloride, TEA-Cocoyl Hydrolyzed Collagen, and Sodium salt of pyroglutamic acid, Polysorbate 20, Fragrance, Methylchloroisothiazalinone and Deionized water; and the second package additionally includes Propylene glycol and PEG-75-Lanolin.

6. The composition of claim 5, wherein percent by weight of additional ingredients in the first package are:

| Trimethylammonium - substituted epoxide | 0.5 |
| Hydroxy ethyl cellulose | 0.06 |
| Propylene Glycol | 8.0 |
| Dicetyl Dimonium Chloride | 0.5 |
| TEA-Cocoyl hydrolyzed collagen | 0.1 |
| Sodium salt of pyroglutamic acid | 0.1 |
| Polysorbate 20 | 0.12 |
| Fragrance | 0.02 |
| Methylchloroisothiazalinone | 0.04 |
| Deionized water | Balance to 1004 | and percent by weight of additional ingredients in the second package are:

| Propylene glycol | 5.0. |
| PEG-75-Lanolin | 4.0 |
| Nonoxynol-10-carboxylic acid- | 1.0. |

7. A method of relaxing hair comprising placing an amount of the composition from the first package of claim 1 in the hair and distributing said composition throughout the hair until it is thoroughly wetted; detangling the hair with a comb; parting the hair into several sections, and applying an amount of the relaxer composition from said second package into each section of parted hair for a sufficient period of time to relax the hair; rinsing the hair free of relaxer; and drying the hair.

8. The method of claim 7, wherein the polyampholyte terpolymer present in the non-alkaline pretreatment composition of said first package is present in an amount from about 5 to about 10% by weight, and the amount of polyampholyte terpolymer in said second package is present in an amount from about 0.5 to about 1.5% by weight.

9. The method of claim 8, wherein the amount of polyampholyte terpolymer is present in amounts of from about 6 to about 9% of said first package, and the amount of polyampholyte terpolymer in said second package is present in an amount from about 0.8 to about 1.2% by weight in the second package.

10. The method of claim 9, wherein the amount of polyampholyte terpolymer is present in the amount of 6% by weight in the first package, and the amount of polyampholyte terpolymer present in the second package is 1.1% by weight.

11. The method of claim 10 wherein the first package additionally includes Trimethylammonium—substituted epoxide, Hydroxy ethyl cellulose, Propylene Glycol, Dicetyl Chloride, TEA-Cocoyl Hydrolyzed Collagen, and Sodium salt of Pyroglutamic acid, Polysorbate 20, Fragrance, Methylchloroisothiazalinone and Deionized water; and the second package additionally includes Propylene glycol and PEG-75-Lanolin.

12. The method of claim 11, wherein the percent by weight of additional ingredients in the first package are:

| Trimethylammonium - substituted epoxide | 0.5 |
| Hydroxy ethyl cellulose | 0.06 |
| Propylene Glycol | 8.0 |
| Dicetyl Dimonium Chloride | 0.5 |
| TEA-Cocoyl Hydrolyzed Collagen | 0.1 |
| Sodium salt of pyroglutamic acid | 0.1 |
| Polysorbate 20 | 0.12 |
| Fragrance | 0.02 |
| Methylchloroisothiazalinone | 0.04 |
| Deionized water | Balance to 100% | and the percent by weight of additional ingredients in the second package are:

| Propyl glycol | 5.0 |
| PEG-75-Lanolin | 4.0 |
| Nonoxynol-10-carboxylic acid | 1.0. |

* * * * *